United States Patent [19]
Hurley et al.

[11] Patent Number: 5,510,709
[45] Date of Patent: Apr. 23, 1996

[54] EDDY CURRENT SURFACE INSPECTION PROBE FOR AIRCRAFT FASTENER INSPECTION, AND INSPECTION METHOD

[75] Inventors: Donna C. Hurley, Albany; Robert S. Gilmore, Burnt Hills; John D. Young, Rexford, all of N.Y.

[73] Assignee: General Electric Company, Schenectady, N.Y.

[21] Appl. No.: 423,489

[22] Filed: Apr. 19, 1995

Related U.S. Application Data

[63] Continuation of Ser. No. 127,269, Sep. 27, 1993, abandoned.
[51] Int. Cl.⁶ .................................................. G01N 27/82
[52] U.S. Cl. ..................... 324/242; 324/241; 324/249; 324/225; 324/235
[58] Field of Search .................................. 324/242, 241, 324/240, 225, 235

[56] References Cited

U.S. PATENT DOCUMENTS

| | | | |
|---|---|---|---|
| 2,555,853 | 4/1945 | Irwin | 324/242 |
| 3,449,664 | 6/1969 | Smith | 324/235 |
| 4,495,466 | 1/1985 | Lankin | 324/242 |
| 4,677,379 | 6/1987 | Arnaud et al. | 324/242 |
| 4,808,927 | 2/1989 | Cecco et al. | |
| 4,849,693 | 7/1989 | Prince et al. | 324/225 |

OTHER PUBLICATIONS

"Special Eddy Current Probes for Heat Exchange Inspection", V. S. Cecco et al., Proceedings of the 8th International Conference on NDE in the Nuclear Industry, Kissimmee, Florida, Nov. 17–20, 1986, pp. 169–174.
"Probe–Flaw Interactions with Eddy Current Array Probes", Bert A. Auld, Review of Progress In Quantitative NDE 10, edited by D. O. Thompson and D. E. Chimenti (Plenum Press, N.Y., 1988), pp. 951–955.
"Flexible Substrate Eddy Current Coil Arrays", Yehuda D. Krampfner et al., Review of Progress in Quantitative NDE 7, edited by D. O. Thompson and D. E. Chimenti (Planum Press, N.Y., 1988), pp. 471–478.
"Advanced Eddy Current Array Defect Imaging", Mirek Macecek, Review of Progress in Quantitative NDE 10, edited by D. O. Thompson and D. E. Chimenti (Plenum Press, N.Y., 1991), pp. 995–1002.
"Detecting Second–Layer Fatigue Cracks Under Installed Skins and Fasteners with Low–Frequency Eddy Current Array", Brian Hill et al., The American Society for Nondestructive Testing, Inc., Materials Evaluation, Dec. 1992.

*Primary Examiner*—Kenneth A. Wieder
*Assistant Examiner*—Kourosh Cyrus Khosravi
*Attorney, Agent, or Firm*—Paul R. Webb, II

[57] ABSTRACT

An eddy current surface inspection array probe and method for detecting cracks and flaws in aircraft skin metal immediately surrounding rivets, without requiring rivet removal or manual scanning. The array probe includes a circular array of small sense coils positioned beneath a much larger drive coil encased in ferrite. The sense coils are differentially connected in pairs such that the signals from two sense coils located on opposite sides of the rivet (180° apart) subtract to produce a resultant output signal. During operation, the probe is positioned concentrically over the rivet and data acquired from all sense coil pairs. If no cracks or other defects are present, all sense coil pairs produce a null (zero) signal. If a crack exists, some sense coil pairs (the exact number depending on the crack length, number of sense coils, and sense coil spacing) produce a non-zero signal. The probe and method can be employed to inspect a variety of other structural features which are nominally circularly symmetrical.

21 Claims, 3 Drawing Sheets

COLL PAIR   A B C D E F G ....

COLL PAIR   A B C D E F G ....

EDDY CURRENT SURFACE INSPECTION PROBE FOR AIRCRAFT FASTENER INSPECTION, AND INSPECTION METHOD

This application is a Continuation of application Ser. No. 08/127,269 filed Sep. 27, 1993, now abandoned.

BACKGROUND OF THE INVENTION

The present invention relates generally to the inspection of structures employing eddy current techniques and, more particularly, to an eddy current probe and method for detecting flaws in structures having features which are nominally circularly symmetrical, such as aircraft skin structures fastened by means of rivets.

The safety and structural integrity of aircraft continues to be of concern to manufacturers as well as consumers. As the average age of aircraft grows, reliable and accurate inspection of all aircraft components becomes increasingly important, especially the aircraft surface and surface fasteners (rivets).. It is thus necessary to detect cracks or other defects located below the aircraft surface, as well as defects located near the rivet.

Ultrasonic and single-probe eddy current techniques have been used for detecting aircraft surface defects near rivets. However, both methods have drawbacks. Ultrasonic signals can be difficult to interpret because of the complicated geometry and number of interfaces. Eddy current inspection may require the removal of the rivet, which is undesirable. In-field inspection is further complicated by factors such as hard-to-reach areas, human fatigue, and rough or uneven surfaces.

By way of further background, eddy current inspection is a commonly used technique for non-destructively detecting discontinuities or flaws in the surface of various components, including aircraft engine parts and aircraft skin surfaces. Very briefly, eddy current inspection is based on the principle of electromagnetic induction. In one approach, a drive coil is employed to induce eddy currents within the material under inspection, and secondary magnetic fields resulting from the eddy currents are detected by a sense coil, generating signals which are subsequently processed for the purpose of detecting flaws.

Eddy current testing for flaws in conductive materials is often done by mechanically scanning a single probe in two dimensions. For example, U.S. patent application Ser. No. 07/772,761, filed Sep. 16, 1991, entitled "An Improved Method for Inspecting Components Having Complex Geometric Shapes" describes methods for interpreting eddy current image data acquired by a single probe, particularly in the context of inspecting a high pressure turbine (HPT) disk dovetail slot.

The single probe scanning method is time consuming. Accordingly, probe arrays have been developed to improve the scanning rate, as well as to increase flaw detection sensitivity, compared to single probe techniques. For example, General Electric High Density Interconnect (HDI) technology has been used to fabricate flexible eddy current probe arrays. In particular, Hedengren et al. application Ser. No. 07/696,455, filed May 5, 1991, the entire disclosure of which is hereby expressly incorporated by reference, discloses a hybrid method of both electronic and mechanical scanning employing an eddy current probe array comprising a plurality of spatially correlated eddy current probe elements disposed within a flexible interconnecting structure which may be employed to collect a discrete plurality of spatially correlated eddy current measurements for non-destructive near surface flaw detection.

HDI fabrication techniques which are advantageously employed in the fabrication of the flexible array structure of the above-incorporated application Ser. No. 07/696,455 are disclosed in Eichelberger et al. U.S. Pat. No. 4,783,695, entitled "Multichip Integrated Circuit Packaging Configuration and Method" and related patents and applications such as Eichelberger et al. application Ser. No. 07/864,786, filed Apr. 7, 1992, which is a continuation of application Ser. No. 07/504,769, filed Apr. 5, 1990, now abandoned, entitled "A Flexible High Density Interconnect Structure and Flexibly Interconnected System", the entire disclosures of which are hereby also expressly incorporated by reference.

Mechanical scanning can be entirely eliminated by employing static scanning and a suitable probe array. Thus, a variety of static scanning approaches have been proposed in the literature, whereby a two-dimensional array of sense elements is placed in a stationary position, and scanning is accomplished by electronically switching between the elements. Examples of this approach are disclosed in the following literature references: Bert A. Auld, "Probe-Flaw Interactions with Eddy Current Array Probes", Review of Progress in Quantitative NDE 10, edited by D. O. Thompson and D. E. Chimenti (Plenum Press, News York, 1991), pages 951–955; Yehuda D. Krampfner and Duane D. Johnson, "Flexible Substrate Eddy Current Coil Arrays", Review of Progress in Quantitative NDE 7, edited by D. O. Thompson and D. E. Chimenti (Plenum Press, New York, 1988), pages 471–478; and Mirek Macecek, "Advanced Eddy Current Array Defect Imaging", Review of Progress in Quantitative NDE 10, edited by D. O. Thompson and D. E. Chimenti (Plenum Press, New York, 1991), pages 995–1002.

In the particular context of the subject invention, the mechanically scanned eddy current probe disclosed in Cecco et al. U.S. Pat. No. 4,808,927, entitled "Circumferentially Compensating Eddy Current Probe with Alternately Polarized Receiver Coil", and in the literature reference V. S. Cecco and F. L. Sharp, "Special Eddy Current Probes for Heat Exchange Inspection", Proceedings of the 8th International Conference on NDE in the Nuclear Industry, Kissimmee, Florida, Nov. 17–20, 1986, pp. 169–174, deserves mention. The Cecco et al. probe is for inspecting tubing from the inside, and employs a large drive coil and an even number of sense coils which are electromagnetically polarized alternately and which are serially connected.

SUMMARY OF THE INVENTION

Accordingly, it is an object of the invention to provide easy-to-use, fast and sensitive probes and methods for detecting cracks and other defects in features which are nominally circularly symmetrical, such as aircraft skin structures immediately surrounding rivets.

It is another object of the invention to provide ,eddy current inspection probes and methods for detecting flaws in aircraft skin structures in the vicinity of a rivet without requiring removal of the rivet.

It is yet another object of the invention to detect signals resulting from defects notwithstanding the presence of signals resulting from rivets.

It is yet another object of the invention to provide an eddy current surface inspection probe and method for detecting flaws in aircraft skin structures surrounding rivets which employs static scanning such that the probe can simply be placed in a stationary position centered over a rivet head.

It is yet another object of the invention to provide such a probe and method which have spatial resolution such that the location of a flaw in aircraft skin material surrounding a rivet is indicated.

Briefly, the invention provides an eddy current surface inspection array probe for detecting flaws in a structure having a feature which is nominally circularly symmetrical about a feature axis, such as a layer of sheet material having a circular aperture, with a rivet within the aperture. The probe of the invention includes a drive coil centered on a probe axis arranged, during inspection, to coincide with the feature axis for inducing an eddy current in the structure. Preferably, to concentrate the magnetic field of the drive coil, the drive coil has a ferrite core, or is formed employing HDI fabrication techniques and has a ferrite backing. The drive coil is of sufficient diameter such that the eddy current is induced in the layer of sheet material and completely surrounds the rivet in-two dimensions, that is, in a plane perpendicular to the feature axis.

The probe additionally includes an even plurality of eddy current sense elements for producing signals in response to the eddy current. The sense elements are arranged in at least one circle, thus defining a circular array, centered on the probe axis, and are organized as associated pairs of sense elements located at diametrically opposed positions on the circle. The sense elements may be arranged in two circles in respective different layers, with the sense elements of one layer staggered with reference to the sense element of the other layer. The sense elements further may be arranged in two circles of different diameters.

The output signal of one sense element of each associated pair is subtracted from the output signal of the other sense element of the pair to produce a resultant signal. Typically, each pair of sense elements comprises a differentially connected pair of coils.

During operation, the probe is placed concentrically over the rivet location, and data is acquired from all sense element pairs. If no cracks or other defects are present, all element pairs produce a null (zero) resultant signal, or at least a signal below a predetermined threshold. (Variations in the material which do not indicate defects may produce relatively small non-zero signals.) If a crack exists, some element pairs (the exact number depending on the crack length, number of elements and element spacing) produce a non-zero signal.

In the preferred embodiments, the probe axis is perpendicular to a surface of the structure during inspection. However, the principles of the invention are applicable to other geometries as well.

The sense element coils of the invention are preferably formed employing HDI fabrication techniques. The sense element coils also may have a ferrite backing layer, or be surrounded by ferrite. Other coil structures may be included as well, for example, absolute-mode coils for liftoff compensation.

Although typically the two coils of each pair are simply differentially connected in series to achieve the subtraction of one output signal from the other output signal, the sense element coils may be individually connected to data acquisition circuitry wherein the output signals are subsequently subtracted, either as analog signals or as digital signals. Thus, an eddy current surface inspection system may be provided which comprises a probe including a drive coil and an even plurality of eddy current sense elements, as described above, as well as data acquisition circuitry electrically connected to the sense elements. The data acquisition circuitry is arranged such that, for each pair of sense elements, the output signal of one sense element of the pair is subtracted from the output signal of the other sense element of the pair to produce a resultant signal.

An eddy current surface inspection method in accordance with the invention for detecting flaws in a structure having a feature which is nominally circularly symmetrical about a feature axis, such as layer of sheet material having a rivet within a circular aperture in the layer of sheet material, includes the steps of positioning a probe such as the probe summarized above adjacent the structure, and then acquiring data from each of the associated pairs of sense elements. The output signal of one sense element of each pair is subtracted from the output signal of the other sense element of the particular pair to produce a resultant signal, and the resultant signals of each of the associated pairs are displayed.

BRIEF DESCRIPTION OF THE DRAWINGS

While the novel features of the invention are set forth with particularity in the appended claims, the invention, both as to organization and content, will be better understood and appreciated, from the following detailed description, taken in conjunction with the drawings, in which:

DETAILED DESCRIPTION

Figure 1:
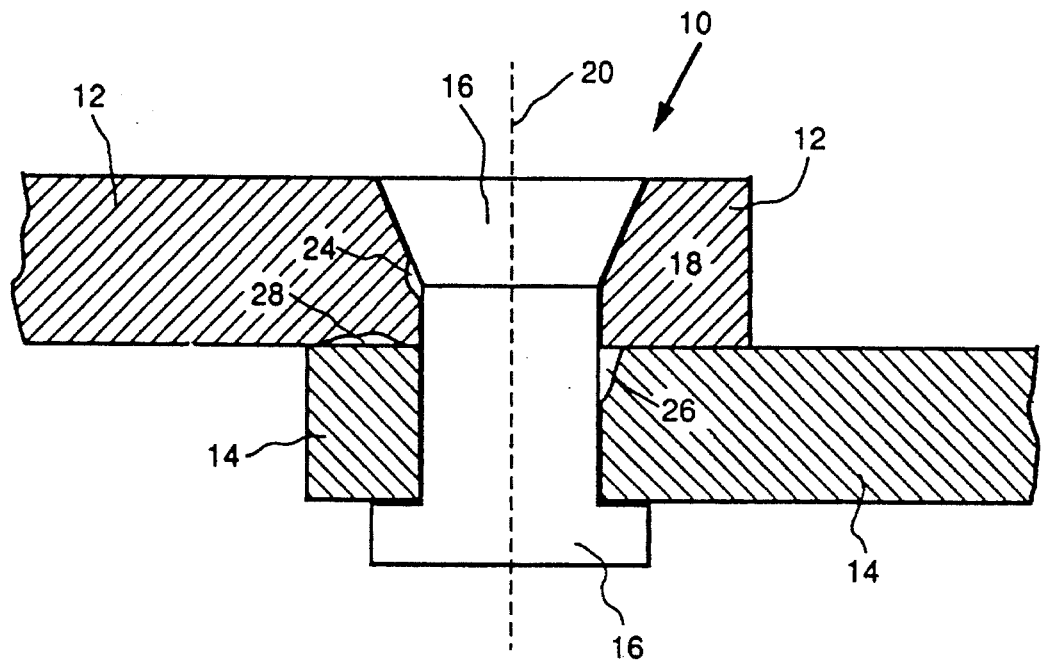
FIG. 1 depicts the geometry of a layer of sheet material secured by means of a rivet.

FIG. 1 depicts the overall geometry of a representative structural feature 10 in the form of a first layer of sheet material 12 secured to a second layer of sheet material 14 by means of a rivet 16. The first layer 12 may comprise, for example, the skin of the aircraft, and the second layer 14 may comprise, for example, a structural support member to which the layer 12 is secured. The layer 12 includes a circular aperture 18 which receives the rivet 16. The structural feature 10 is nominally (in the absence of flaws) circularly symmetrical about a feature axis 20. In the particular geometry depicted, the feature axis 20 is perpendicular to a surface 22 of the layer 12.

FIG. 1 additionally depicts two representative defects 24 and 26 comprising cracks in the layer 12 and 14 respectively. Such cracks 24 and 26 are representative of typical defects which may result, in time, due to metal fatigue. There are however other potential defects or flaws which can occur. For example, corrosion between the layers 12 and 14 can result in a loss of metal such as is represented by region 28.

The defects 24 and 26 are difficult to detect employing conventional techniques because they are located below the surface of the layer 12 and, additionally, are located immediately adjacent the rivet 16.. While ultrasonic inspection techniques may be employed, ultrasonic signals in this situation can be difficult to interpret due to the complicated geometry, as well as the number of interfaces.

Conventional eddy current inspection is greatly complicated by the presence of the rivet 16 immediately adjacent the flaws 24 and 26, and eddy current edge signals resulting from the interface between the layers 12 and 14 and the rivet 16 typically produce large signals inherent in the geometry, tending to mask signals resulting from flaws, such as the cracks 24 and 26. Thus, conventional eddy current inspection may require the removal of the rivet 16, which is highly undesirable.

Figure 2:
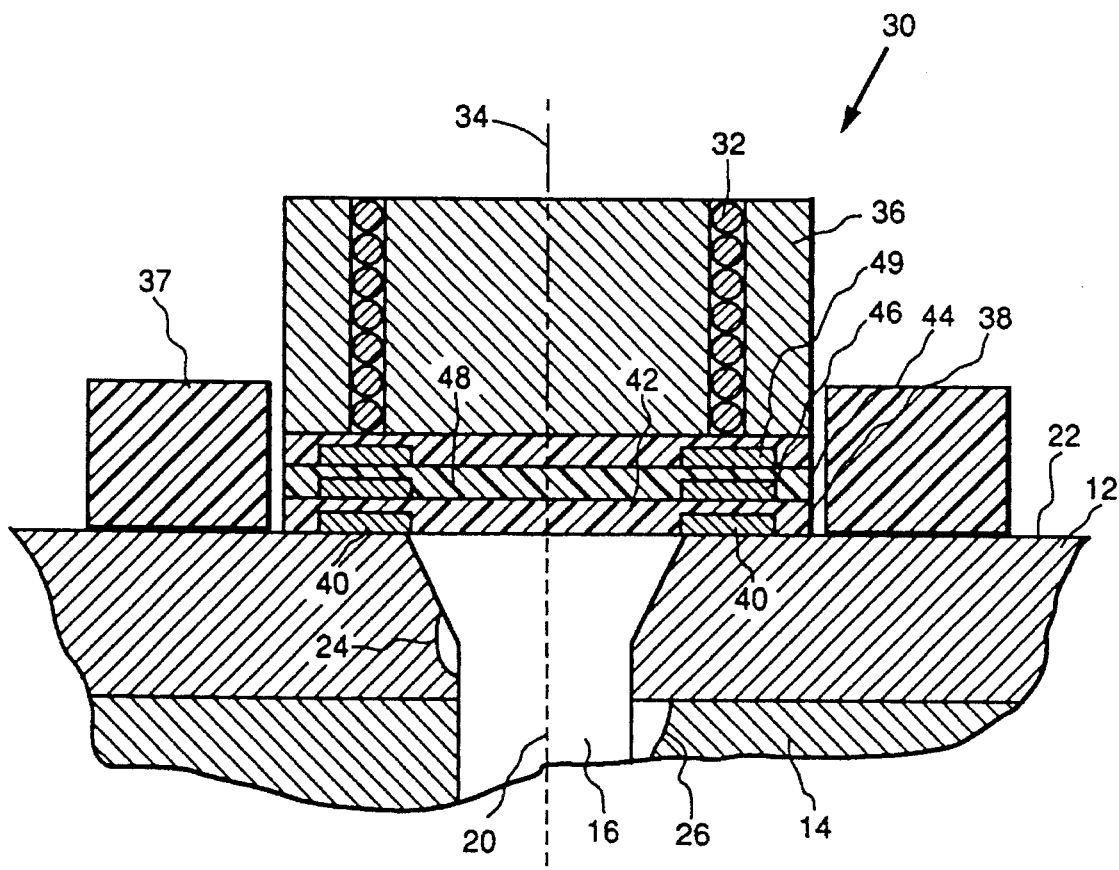
FIG. 2 is a cross-sectional view depicting an eddy current array probe of the invention in position over the rivet of FIG. 1 for inspection.

In accordance with the invention, it is recognized that the circular symmetry of the structural feature 10 may be employed to advantage. Thus FIG. 2 depicts an eddy current array probe 30 which includes a transmit or "drive" coil 32 comprising a multiple-turn solenoid centered on a probe axis 34 arranged to coincide with the feature axis 20 during inspection. The drive coil 32 is of sufficient diameter such that the eddy current is induced in the layers 12 and 14, and completely surrounds the rivet 16. The drive coil 32 thus induces an eddy current in the structure 10. In the particular geometry illustrated, the solenoid 32 and the probe axis 34 are perpendicular to the surface 22 of the layer 12 containing the rivet 16.

Preferably, in order to concentrate the resultant magnetic field down towards the metal surface, the drive coil 32 includes a ferrite core 36 of suitable configuration. In the particular geometry of FIG. 2, the drive coil 32 is in effect encased within the ferrite core 36. The drive coil 32 is fabricated employing any suitable technique, such as by wrapping small-gauge wire around a form for a ferrite coil. Alternatively, the drive coil 32 may be formed employing HDI fabrication techniques, with a ferrite backing layer included.

During use, the probe 30 is centered on a rivet 16. A centering aid, such as a transparent jig 37 with a sliding fit to the probe 30 may be employed.

During operation, the drive coil 32 is energized with alternating current, at one or more frequencies within the range, for example, of 1 kHz to 1 MHz, which induces circular currents in the nearby metal surfaces of the nominally circular symmetrical structural feature 10. The presence of cracks or other defects perturbs the circular flow of the eddy current.

This current perturbation is detected by smaller eddy current sense elements comprising a sense element array in the form of a first layer 38 of receive coils 40.

The receive coils 40 are supported on or within a layer 42 of polyimide material, and are fabricated employing the HDI array technology disclosed in detail in the above-incorporated application Ser. No. 07/696,455, which is in turn based on the flexible HD fabrication techniques of the above-incorporated application Ser. No. 07/865,786, and briefly described hereinbelow.

The array probe 30 may also include a second layer 44 of eddy current receive coils 46, likewise supported on or within a layer 48 of polyimide, and also comprising part of a structure formed employing HDI fabrication techniques. In this case, the overall receive coil configuration comprises the two layers 38 and 44 of coils 40 and 46 staggered such that the most sensitive areas of one layer 38 coincide with the least sensitive areas of the other layer 44. Also, the receive coils 40 and 46 may be provided with a ferrite backing layer or layers, be surrounded with ferrite, or both.

Although the representation of FIG. 2 suggests there is just one layer per receive or sense coil, this is a representation only. In practice, each of the receive or sense coils 40, 46 may be a multilayer coil.

Other layers may be formed in the coil structure such as single, absolute-mode coils 49 to measure variations in probe-metal separation (liftoff), to accordingly compensate the differential signals.

As disclosed in Eichelberger et al. U.S. Pat. No. 4,783,695, and related patents and applications such as Ser. No. 07/864,786, the high density interconnect structure developed by General Electric Company has previously offered many advantages in the compact assembly of electronic systems. For example, an electronic system such as a microcomputer which incorporated between thirty and fifty chips, or even more, can be fully assembled and interconnected on a single substrate which is two inches long by two inches wide by 50 mils thick. This structure is referred to herein as an "HDI structure", and the various previously-disclosed methods for fabricating HDI structures are referred to herein as "HDI fabrication techniques".

Very briefly, in typical systems employing this high density interconnect structure, a ceramic substrate is provided, and individual cavities or one large cavity having appropriate depths at the intended locations of the various chips are prepared. Various components are placed in their desired locations within the cavities and adhered by means of a thermoplastic adhesive layer.

A multi-layer high density interconnect (HDI) overcoat structure is then built up to electrically interconnect the components into an actual functioning system. To begin the HDI overcoat structure, a polyimide dielectric film, which may be Kapton® polyimide available from I. E. du Pont de Nemours Company, about 0.005 to 0.003 inch (12.5 to 75 microns) thick is pretreated to promote adhesion and coated on one side with ULTEM® polyetherimide resin or another thermoplastic and laminated across the top of the chips, other components and the substrate, with the ULTEM® polyetherimide resin or another thermoplastic and laminated across the top of the chips, other components and the substrate, with the ULTEM® resin serving as a thermoplastic adhesive to hold the Kapton® film in place. Exemplary lamination techniques are disclosed in Eichelberger et al. U.S. Pat. No. 4,933,042.

The actual as-placed locations of the various components and contact pads thereon are determined, typically employing optical imaging techniques. Via holes are adaptively laser drilled in the Kapton® film and ULTEM® adhesive layers in alignment with the contact pads on the electronic components in their actual as-placed positions. Exemplary laser drilling techniques are disclosed in Eichelberger et al. U.S. Pat. Nos. 4,714,516, and 4,894,115; and in Loughran et al. U.S. Pat. No. 4,764,485.

A metallization layer is deposited over the Kapton® film layer and extends into the via holes to make electrical contact to the contact pads disposed thereunder. This metallization layer may be patterned to form individual conductors during the process of depositing it, or may be deposited as a continuous layer and then patterned using photoresist and etching. The photoresist is preferably exposed using a laser which, under program control, is scanned relative to the substrate to provide an accurately aligned conductor pattern at the end of the process. Exemplary techniques for patterning the metallization layer are disclosed in Wojnarowski et al. U.S. Pat. Nos. 4,780,177 and 4,842,677 and in Eichelberger et al. U.S. Pat. No. 4,835,704 which discloses an "Adaptive Lithography System to Provide High Density Interconnect". Any misposition of the individual electronic components and their contact pads is compensated for by an adaptive laser lithography system as disclosed in U.S. Pat. No. 4,835,704.

Typical such systems, being formed on a ceramic substrate, are not flexible. However, the above-incorporated Eichelberger et al. application Ser. No. 07/865,786 discloses techniques for making at least portions of the high density interconnect structure flexible.

Figure 3:
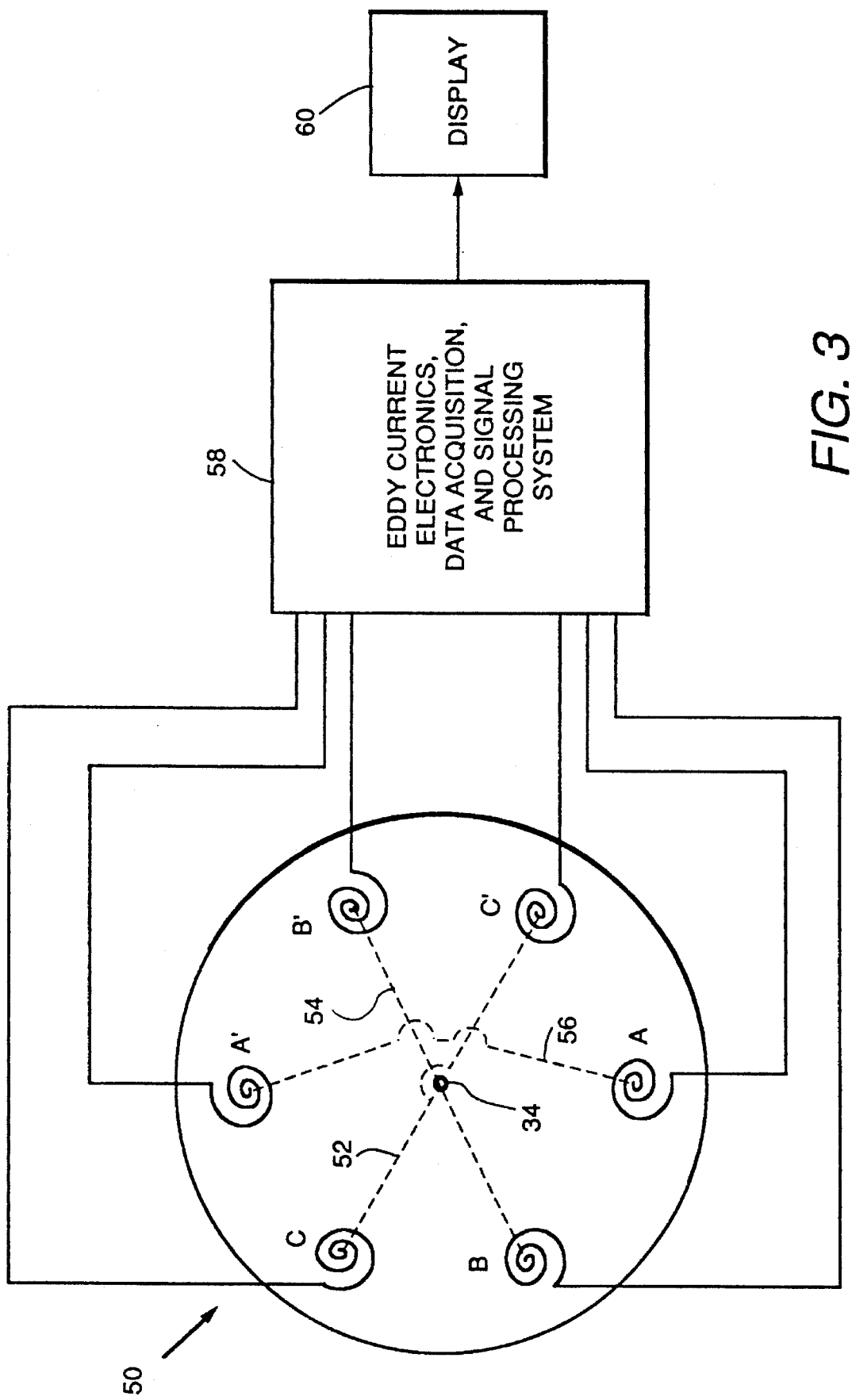
FIG. 3 is a highly schematic depiction of the eddy current sense elements of the FIG. 2 array probe connected to a data acquisition system.

Referring now to FIG. 3, in addition to FIG. 2, FIG. 3 includes a simplified representation 50 of one of the layers 38, 44 of sense elements 40, 46 of FIG. 2. In FIG. 3, the eddy current sense elements are even in number and comprise associated pairs A,A', B,B' and C,C' arranged in a circle centered on the probe axis 34. The sense element coils of each pair are located at diametrically opposed positions on the circle, that is, 180° apart. The actual number of sense element pairs A, A', B, B', C, C', etc., is selected based on the desired spatial resolution. For example, thirty-six pairs would provide data every 5°. Typically, the number of pairs is within a range of from eight to sixty-four, although the invention is not limited to any particular number of sense element pairs.

In accordance with the invention, the arrangement is such that the output signal of one sense element of each pair is subtracted from the output signal of the other sense element of the pair to produce a resultant signal. In FIG. 3, this is achieved simply by electrically connecting the two sensor coils of each pair in series, in the manner of a differential pair, such that the two signals are subtracted from each other to produce a resultant signal. An alternative description is that the two coils of each pair are connected in series, but are wound in opposition, that is, in the opposite sense compared to each other. If both coils of the particular pair sense the same eddy current signal, which occurs in the event the structural feature is perfectly circularly symmetrical and has no defects, the resultant output signal is null or zero.

Thus, in operation, the probe 30 is placed concentrically over the rivet 16, and data acquired from all sense elements or sense element pairs. If no cracks or other defects are present, all element pairs produce a null or zero signal, or at least signals which are below a predetermined threshold established such that variations in the material which do not indicate defects may be disregarded. If a crack or defect exists, such as the cracks 24 and 26, some element pairs (the exact number depending upon the crack length, number of elements and element spacing, etc.) produce a non-zero signal.

As noted above, the coil pairs are preferably fabricated employing HDI fabrication techniques as described in the various patents and patent applications referenced hereinabove. It will be appreciated that, in order to avoid short circuits, interconnection conductors 52, 54 and 56 are in different layers within the HDI structure, and that vias (not shown) are appropriately formed in order to achieve electrical continuity between the various layers.

In FIG. 3, the representative structure 50 is shown connected to a box 58 representative of eddy current electronics and a data acquisition and signal processing system 58. As is conventional, the eddy current electronics within the box 58 includes amplifiers and circuitry for quadrature detection. The data acquisition and signal processing system within the box 58 may include elements such as analog-to-digital convertors and memory. Although not shown in FIG. 3, there is also provided suitable circuitry, including a frequency synthesizer, for supplying drive signals at various frequencies to the drive coil 32.

Preferably, the circuitry within the box 58 is connected to drive a suitable display 60 to present a meaningful indication to an operator. The signals from the sense elements 40, 46 have two components, expressed for example as a real and an imaginary part (or alternatively as magnitude and phase), and typically only one component is used for display and analysis. Usually circuitry is included to "rotate" the signal so that the selected component maximizes signals resulting from defects and flaws, while minimizing extraneous signals.

Figure 4:
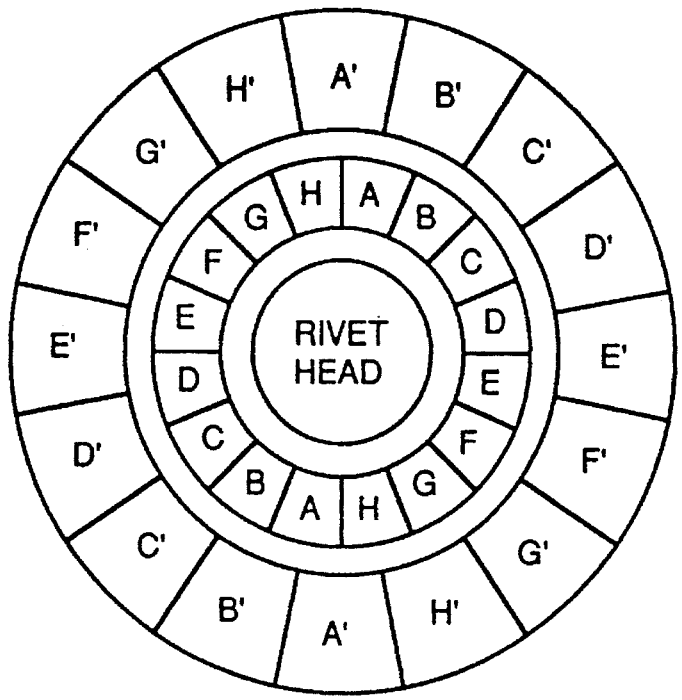
FIG. 4 is another highly schematic view representing a top view of the eddy current sense coils of the FIG. 2 eddy current array probe.

FIG. 4, which may be compared to the representation 50 of FIG. 3, schematically depicts in greater detail a more particular arrangement of sense element pairs, arranged in two concentric rings, with reference to the rivet 16.

Figure 5:
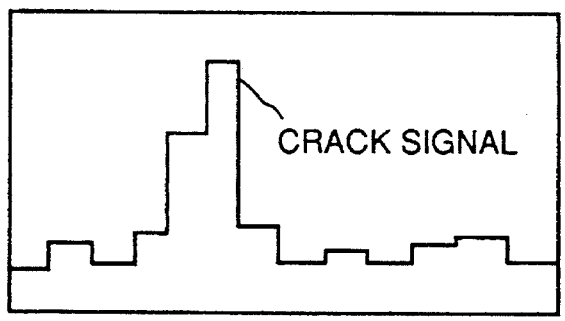
FIG. 5 represents a display of signals from an array probe with the array probe in one angular position.
Figure 6:
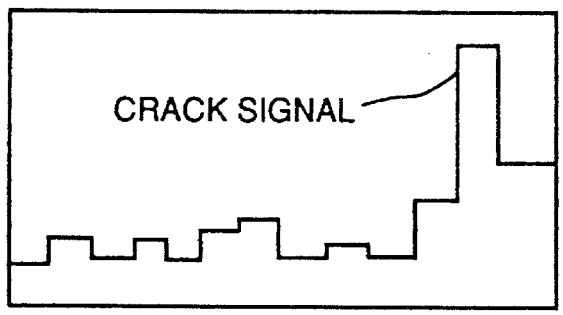
FIG. 6 represents a display of signals with the array probe in a different angular position.

FIGS. 5 and 6 depict, by way of example, one form of data display which may be generated for viewing by the operator on the FIG. 6 display 60. FIGS. 5 and 6 depict the resultant signals from each sensor pair around the rivet circumference. If the probe 30 is angularly rotated, and data acquired for the resultant different probe orientations, crack signals appear to "slide" across the display. Moreover, as noted above, circuitry may serve to "rotate" the signals. Although the probe and method of the subject invention may be employed in a purely static manner, such rotation of the probe is preferred in order to eliminate the possibility of missing a crack signal at the edge of the display, and to ensure complete inspection coverage. If necessary, further data analysis or processing to detect defects can be performed, and the data can be stored to serve as a record of the rivet inspection.

In some circumstances, the inspection may be repeated at various drive frequencies, or data may be acquired from different sense elements at different frequencies. For example, the coils 49 for lift off compensation may perform better at a different frequency than the coils 40 and 46 used for defect detection. In addition, multi-frequency data from sensor elements can be combined to provide additional information, such as discrimination between cracks and surface scratches.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. An eddy current surface inspection probe for detecting flaws in a structure having a feature which is nominally circularly symmetrical about a feature axis, said probe comprising:

a drive coil centered on a probe axis arranged to coincide with the feature axis during inspection for inducing an eddy current in the structure;

an even plurality of eddy current sense elements for producing signals in response to the eddy current, said sense elements being arranged in at least one circle centered on said probe axis and organized as a plurality of associated pairs of sense elements located at diametrically opposed positions on said at least one circle; and a plurality of interconnecting means, each associated with one of said pairs, the interconnecting means associated with a given pair comprising means for electrically interconnecting the sense elements of the given pair such that the output signal of one sense element of the given pair is subtracted from the output signal of the other sense element thereof to produce a data signal, said interconnecting means being electrically isolated from one another to cause each of said pairs to produce a separate data signal.

2. The probe in accordance with claim 1, wherein each pair of sense elements comprises a differentially connected pair of coils.

3. The probe in accordance with claim 1, wherein;
said probe includes at least three of said associated pairs of sense elements.

4. The probe in accordance with claim 1, wherein said sense elements are arranged in two circles in respective different layers, the sense elements of one layer being staggered with reference to the sense elements of the other layer.

5. The probe in accordance with claim 1, wherein said sense elements are arranged in two circles of different diameters.

6. The probe in accordance with claim 1, wherein said drive coil has a ferrite core.

7. The probe in accordance with claim 1, which is for detecting flaws in a structure having at last one layer of sheet material, a circular aperture in said layer of sheet material, and a rivet within the aperture, wherein
said drive coil is of sufficient diameter such that the eddy current is induced in the at least one layer of sheet material and completely surrounds the rivet in two dimensions.

8. The probe in accordance with claim 7, wherein said at least one circle of sense elements surrounds the rivet.

9. The probe in accordance with claim 1, which further comprises a liftoff compensation coil.

10. An eddy current surface inspection system for detecting flaws in a structure having a feature which is nominally circularly symmetrical about a feature axis, said system comprising:
a probe including:
a drive coil centered on a probe axis arranged to coincide with the feature axis during inspection for inducing an eddy current in the structure, and
an even plurality of eddy current sense elements for producing signals in response to the eddy current, said sense elements being arranged in at least one circle centered on said probe axis and organized as a plurality of associated pairs of sense elements located at diametrically opposed positions on said at least one circle;
data acquisition circuitry for producing a separate resultant signal for each of said pairs, said data acquisition circuitry being arranged such that, for each pair of sense elements, the output signal of one sense element of the pair is subtracted from the output signal of the other sense element of the pair to produce the resultant signal corresponding to the pair; and
means for providing separate electrical paths between said data acquisition circuitry and each of said pairs of sense elements.

11. A system in accordance with claim 10, which is arranged such that said probe axis is perpendicular to a surface of the structure during inspection.

12. A system in accordance with claim 10, wherein said sense elements are arranged in two circles in respective different layers, the sense elements of one layer being staggered with reference to the sense elements of the other layer.

13. A system in accordance with claim 10, wherein said sense elements are arranged in two circles of different diameters.

14. A system in accordance with claim 10, wherein said drive coil has a ferrite core.

15. A system in accordance with claim 10, which is for detecting flaws in a structure having at least one layer of sheet material, a circular aperture in said layer of sheet material, and a rivet within the aperture, wherein
said drive coil is of sufficient diameter such that the eddy current is induced in the at least one layer of sheet material and completely surrounds the rivet in two dimensions.

16. A system in accordance with claim 15, wherein said at least one circle of sense elements surrounds the rivet.

17. A system in accordance with claim 10, which further comprises a liftoff compensation coil.

18. An eddy current surface inspection method for detecting flaws in a structure having a feature which is nominally circularly symmetrical about a feature axis, said method comprising:
positioning a probe in adjacent relationship with the structure, so that an axis of the probe is in coinciding relationship with the feature axis, the probe including a drive coil centered on the probe axis for inducing an eddy current in the structure, and an even plurality of eddy current sense elements for producing signals in response to the eddy current, the sense elements being arranged in at least one circle centered on the probe axis and organized as .a plurality of associated pairs of sense elements located at diametrically opposed positions on the at least one circle;
acquiring a separate resultant signal from each of the associated pairs of sense elements, the output signal of one sense element of a given pair being subtracted from the output signal of the other sense element of the given pair to produce the resultant signal for the given pair; and
maintaining said coinciding relationship between said probe axis and said feature axis until said acquiring step has been completed.

19. A method in accordance with claim 18, which further comprises simultaneously displaying the resultant signals of two or more of the associated pairs.

20. A method in accordance with claim 18, which is for detecting flaws in a structure having at least one layer of sheet material, a circular aperture in said layer of sheet material, and a rivet within the aperture, which method comprises employing a probe wherein the drive coil is of sufficient diameter such that the eddy current is induced in the at least one layer of sheet material and completely surrounds the rivet.

21. A method in accordance with claim 20, which comprises employing a probe wherein the at least one circle of sense elements surrounds the rivet.

* * * * *